United States Patent [19]
Lee

[11] Patent Number: 5,935,870
[45] Date of Patent: Aug. 10, 1999

[54] TOP VIEW TEM SAMPLE PREPARATION METHOD

[75] Inventor: Jeng-Hang Lee, King-Ching Town, Taiwan

[73] Assignee: Taiwan Semiconductor Manufacturing Company, Ltd., Hsin-Chu, Taiwan

[21] Appl. No.: 09/079,883

[22] Filed: May 15, 1998

[51] Int. Cl.[6] ................................................. H01L 21/304
[52] U.S. Cl. ........................ 438/692; 438/693; 438/704; 438/706
[58] Field of Search ................................. 438/692, 693, 438/706, 704; 156/345

[56] References Cited

U.S. PATENT DOCUMENTS

| | | | |
|---|---|---|---|
| 4,885,051 | 12/1989 | Hwang et al. | 156/345 |
| 4,920,076 | 4/1990 | Holland et al. | 437/238 |
| 4,939,364 | 7/1990 | Ishitani et al. | 250/309 |
| 5,009,743 | 4/1991 | Swann | 156/643 |
| 5,093,572 | 3/1992 | Hosono | 250/310 |
| 5,270,552 | 12/1993 | Ohnishi et al. | 250/307 |
| 5,637,530 | 6/1997 | Gaines et al. | 114/105 |
| 5,841,931 | 11/1998 | Foresi et al. | 385/131 |
| 5,897,353 | 4/1999 | Kim et al. | 438/261 |

*Primary Examiner*—Benjamin Utech
*Assistant Examiner*—Kin-Chan Chen
*Attorney, Agent, or Firm*—George O. Saile; Stephen B. Ackerman

[57] ABSTRACT

A method for preparing a sample for TEM is described. The method is particularly well suited for examining the active region of an FET. After removing the various layers present above the active region, the polysilicon gate is exposed and then selectively removed. In a key feature of the invention, care is taken to ensure that the regions of field oxide on either side of the active region are left fully intact. After using a laser to mark the area of interest for later ease of identifcation, the silicon is etched down to a few thousand Angstroms, followed by ion milling to further reduce the thickness over the area of interest. Because of the support provided by the field oxide, very thin layers can be exposed without the danger of them pulling away from the silicon.

16 Claims, 3 Drawing Sheets

TOP VIEW TEM SAMPLE PREPARATION METHOD

FIELD OF THE INVENTION

The invention relates to the general field of transmission electron microscopy with particular reference to preparing the active region of a field effect transistor for examination.

BACKGROUND OF THE INVENTION

Transmission Electron Microscopy (TEM) is a widely used technique for examining a very small area at a particular depth within a specimen. A common example, of particular interest in the context of the present invention, is the thin layer of insulation that underlies the gate of a field effect transistor (FET). Examination of this area (known as the active region of the transistor) needs to be performed after the full device has been fabricated since defects may have been introduced into the active area as a result of the fabrication process itself.

A specimen suitable for TEM needs to be between about 200 and 5,000 Angstroms thick. With this in mind, it is first ground down to a thickness that is just sufficient to retain its mechanical integrity. A small portion may then be removed and attached to a suitable holder which then allows it to be further thinned down or the full specimen may be attached to a suitable support. Thinning then proceeds in a limited area within which the area of interest for TEM lies. Material removal in such small areas is usually achieved by means of ion milling which allows the controlled removal of material down to thicknesses of a few hundred Angstroms.

The present invention uses the second of the above two methods. However, in the case of performing TEM on the active region of an FET it has been found that this method, as described above, often fails because the gate oxide that is to be examined separates from the main body of the specimen and falls away. The present invention is directed to providing a method of TEM specimen preparation that is free of this problem.

We have been unable to find any prior art that teaches the approach used by the present invention. Several references were, however, found to be of interest. For example, Hosono (U.S. Pat. No. 5,093,572 March 1992) describes a method of combining both focussed ion beams (FIB) and scanning electron microscopy (SEM) in the same apparatus. This makes it possible to observe the progress of an ion milling operation without having to interrupt it.

Ohnishi et al. (U.S. Pat. No. 5,270,552 Decmeber 1993) teach a process for partially milling out a tiny section of a relatively large specimen. A probe is then brought in contact with the specimen and bonded to it by means of a tungsten layer that is selectively deposited in the probe's immediate vicinity, using a combination of chemical vapor deposition (CVD) and local heating. Once the probe has bonded to the main specimen, an additional milling step frees the section, making it available for TEM.

Ishitani et al. (U.S. Pat. No. 4,939,364 July 1990) are concerned with preventing the bombarding ions from aggregating or segregating on a surface being processed by an ion beam. Rules for choosing the ion species are given and use of a mass spectrometer to monitor the extent of this problem is described.

Swann (U.S. Pat. No. 5,009,743 April 1991) supplements an ion beam with a directed jet of a reactive gas. The specimen being milled is also heated. This results in high milling rates for beams at near normal incidence.

SUMMARY OF THE INVENTION

It has been an object of the present invention to provide a method for preparing a specimen for transmission electron micros-copy.

Another object of the invention has been to prepare, for TEM, portions of an integrated circuit, particularly the active region of a field effect transistor.

Yet another object has been to provide a method to ensure that said active region remains in place at the conclusion of specimen preparation.

These objects have been achieved by first removing the various layers present above the active region until the polysilicon gate over said region is just exposed, so that it can then be selectively removed. In a key feature of the invention, care is taken to ensure that the regions of field oxide on either side of the area of interest are left fully intact. After using a laser to mark the area of interest for later ease of identifcation, the silicon is etched down to a few thousand Angstroms, followed by ion milling to further reduce the thickness over the area of interest. Because of the support provided by the field oxide, very thin layers can be exposed without the danger of them pulling away from the silicon.

DESCRIPTION OF THE PREFERRED EMBODIMENTS

Figure 1:
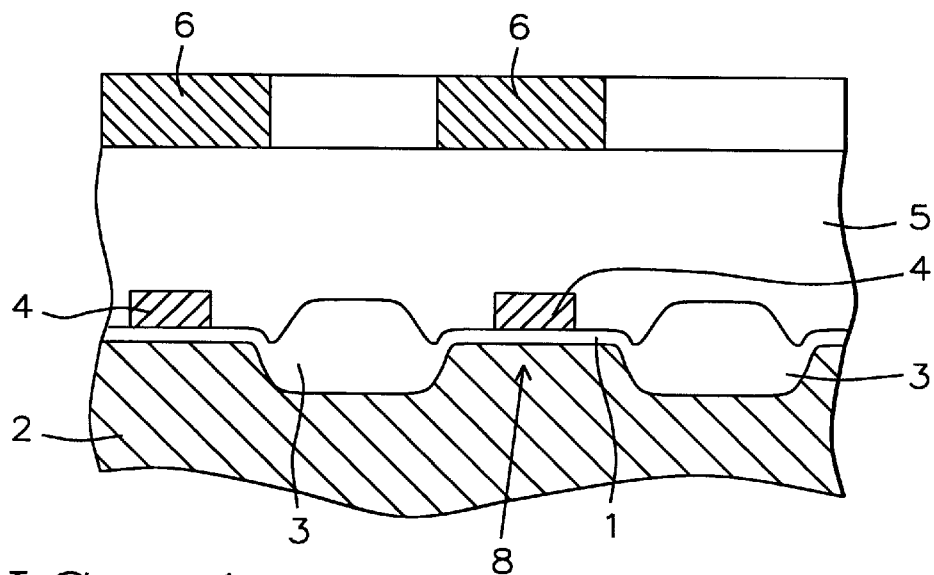
FIG. 1 is a cross-section of part of an integrated circuit, including an area that is to be examined using TEM.

Referring now to FIG. 1, a schematic cross-section is shown of a portion of an integrated circuit. A layer of gate oxide 1 has been grown at the surface of silicon substrate 2. A polysilicon gate 4 sits atop the gate oxide and is separated and electrically isolated from adjoining gates by regions of field oxide 3. The latter are typically between about 0.2 and 0.4 microns thick and occupy areas between about 0.3 and 1 microns wide.

Covering the gates, the gate oxide and the field oxide is dielectric layer 5 which is typically silicon oxide although other dielectric materials such as silicon nitride could also have been used. Shown on the top surface of layer 5 is a portion of a metallic wiring pattern 6. It is in Damascene format in this particular illustration but this has no bearing on the present invention. In most cases there would also be present a number of other features such as spacers on the gates, source and drain regions, and so on, but these are not shown since they do not have any bearing on the practice of the present invention whose purpose is to prepare a sample, such as seen in FIG. 1, so that a suspected defect in the gate oxide (pointed to by arrow 8) can be examined by means of TEM.

Figure 2:
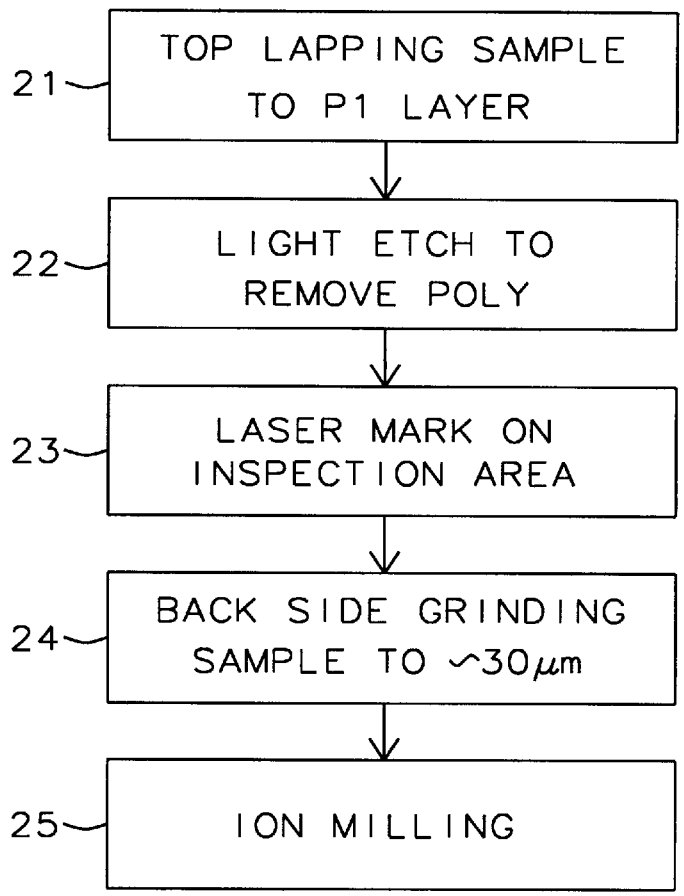
FIG. 2 is a flow chart that gives a brief overview of the process of the present invention.
Figure 3:
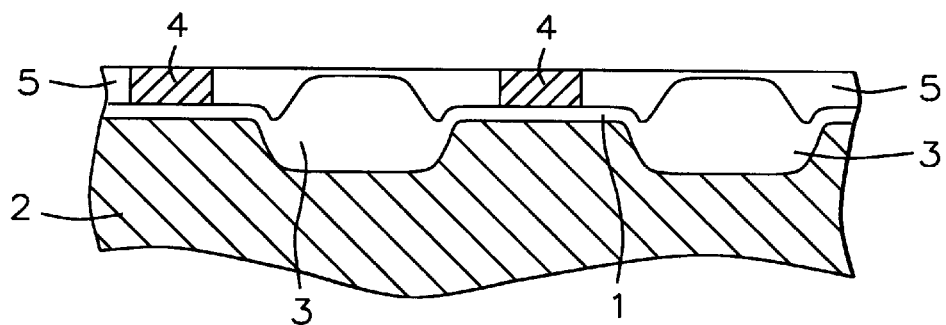
FIGS. 3 and 4 illustrate the removal of material that covers the area of interest for TEM.

Referring now to FIG. 3, the method of the present invention begins with the removal of metal layer 6 followed by the etching of dielectric layer 5 until polysilicon gates 4 are just exposed. This step is reflected in box 21 of the summary flow chart shown in FIG. 2. In a key feature of the invention, care is taken to ensure that the field oxide regions 3 are not affected by the etching which is usually (but not necessarily) accomplished through chemical mechanical etching. It is desirable (though not essential) that a small amount of dielectric layer 5 remain over the field oxide.

Figure 4:
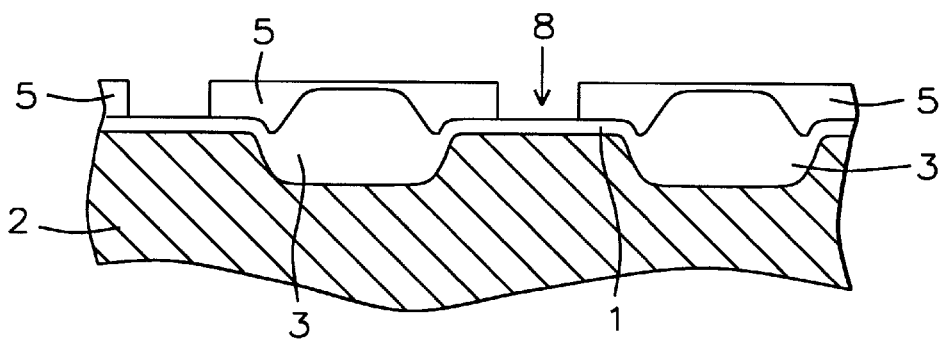

With the polysilicon gates exposed, they can now be selectively removed by etching in a polysilicon etcher for between about 10 and 15 seconds at a temperature of about 25° C., it being critical that both the gate oxide 1 and the field oxide 3 remain in place (see box 22 in FIG. 2). The appearance of the structure at this stage is illustrated in FIG. 4. In order to be able to easily locate the area to be examined under TEM, as pointed to by arrow 8, it is convenient at this stage to make several marks on the gate oxide that surround the suspected location. These marks are made using a laser (not shown) such as a Green Laser operated at a power level between about 100 and 200 watts and having a spot size between about 2 and 5 microns (see box 23 in FIG. 2).

Figure 5:
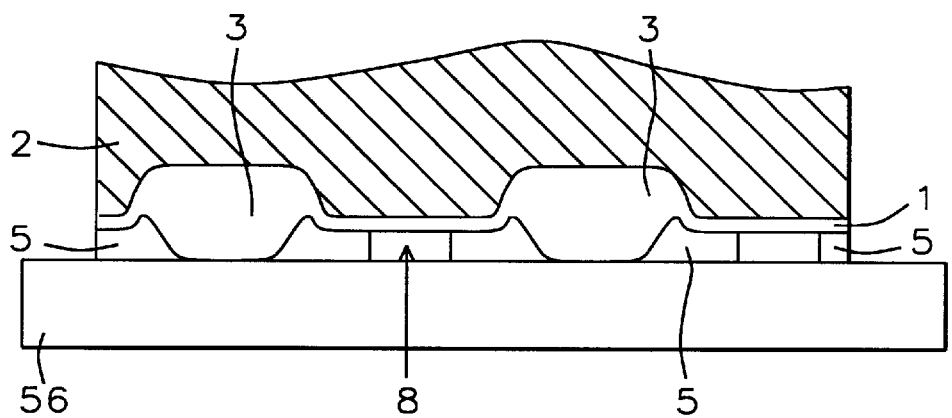
FIGS. 5, 6, and 7 illustrate how the silicon substrate, upon which the area of interest lies, is thinned down to a thickness suitable for the application of TEM.

Referring now to FIG. 5, the structure is attached to a sheet of glass (between about 1 and 3 mm. thick) at dielectric layer 5 and/or the field oxide areas. The attachment of the sheet of glass is accomplished by heating it to a temperature between about 100 and 150° C., which is sufficient to melt a glue such as a wax, and then allowing the molten glue to spread over a surface of the glass. Said coated surface of the glass sheet is then pressed against the dielectric layer, following which both the specimen and the glass are allowed to cool so that the glue hardens.

Figure 6:
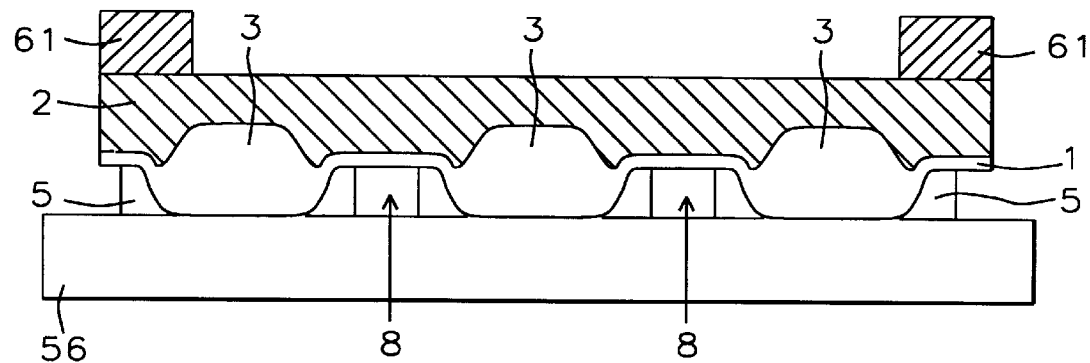

Referring now to FIG. 6, silicon substrate 2 is now etched using chem. mech. polishing until its thickness has been reduced to between about 30 and 40 microns (see box 24 in FIG. 2). Then, metal ring 61 is attached to the silicon so that the marks surrounding the area of interest (arrow 8) are not covered by the ring. Our preferred material for the ring has been copper because of low cost but other metals such as molybdenum could also have been used. The ring has an outer diameter between about 2.5 and 3.5 mm. and an inner diameter between about 1 and 2 mm. It is attached to the silicon by AB glue.

Figure 7:
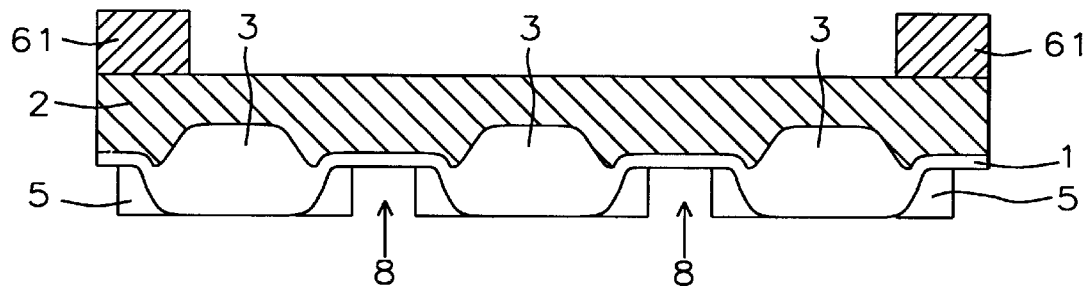

With the ring firmly in place, the sheet of glass 56 can now be removed. This is done by heating the glass to a temperature between about 100 and 125° C. which melts the glue and allows the glass and the specimen to be separated. Any residual traces of glue left on the specimen are readily removed by the application of acetone. At this point the structure has the appearance illustrated in FIG. 7.

Figure 8:
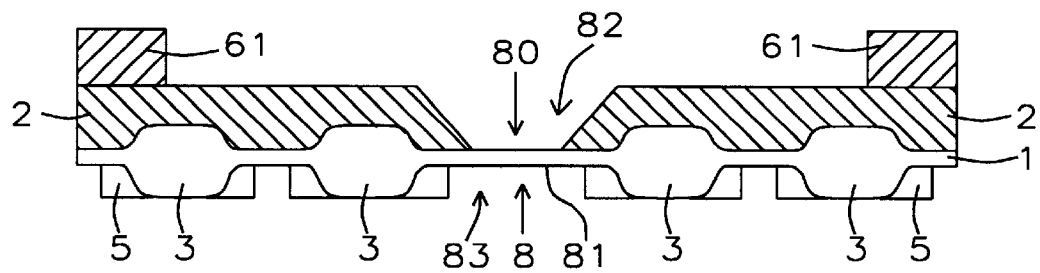
FIG. 8 is a cross-section of a specimen immediately after ion milling and ready for TEM.

At this stage the thickness of silicon 2 is about 30 microns. In order to remove as much as possible of the silicon that is directly over the laser marks, ion milling is used (see box 25 in FIG. 2). This allows controlled removal of silicon from a region above and surrounding the laser marks, thus forming a cavity 82 within which the defect to be examined by TEM lies. This is illustrated in FIG. 8. Ion milling is accomplished by means of a beam of argon ions, focussed down to an area between about 0.1 and 0.3 sq. mm. at a current level between about 10 and 30 microamps. Milling generally takes between about 10 and 40 minutes.

Once the requisite amount of silicon has been removed, the specimen is ready for TEM which will be effected by passing an electron beam such as 80 through the area of interest. Note that, in practice, the center of web 81 (freestanding portion of layer 1) may be destroyed during ion milling so it is common practice to arrange the ion milling so that the area to be examined is slightly off center (as, for example, pointed to by arrow 83).

Figure 9:
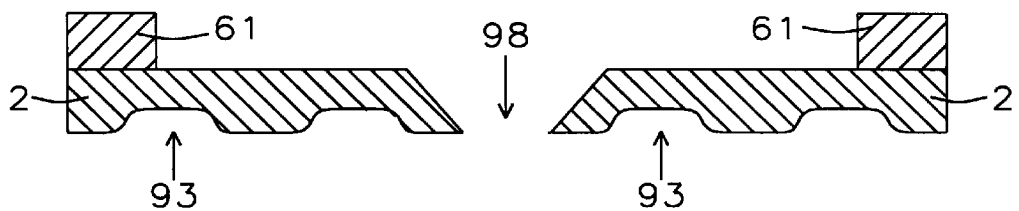
FIG. 9 shows how the area of interest may become separated from the specimen if field oxide is not left in place to provide support for it.

As noted earlier, a key feature of the present invention is that, during specimen preparation, care is taken to ensure that the field oxide regions, between which the area to be examined under TEM is located, are always left intact. If this is not done, and signicant amounts of field oxide are removed, the remaining field oxide often falls away, together with the gate oxide layer that contains the area of interest. The appearance of a specimen that has been subject to this type of mishap is illustrated in FIG. 9. Instead of a layer of gate oxide, all that remains is opening 98 while the regions of field oxide that would have supported the gate oxide have been replaced by cavities, such as 93.

While the invention has been particularly shown and described with reference to the preferred embodiments thereof, it will be understood by those skilled in the art that various changes in form and details may be made without departing from the spirit and scope of the invention.

What is claimed is:

1. A method to prepare a sample for TEM, comprising the sequential steps of:

providing an integrated circuit on a silicon wafer, including a layer of gate oxide on the silicon, at least two areas of field oxide, at least one polysilicon gate, said gate being located between the areas of field oxide, a layer of a dielectric over the gate oxide, the field oxide and the polysilicon gate, and a layer of a metal over the dielectric;

removing the metal layer and then etching the dielectric layer until the polysilicon gate is exposed while leaving all of the field oxide in place;

selectively removing all exposed polysilicon while leaving all of the gate oxide and field oxide in place;

making marks on the gate oxide, said marks placed so as to surround a location to be examined using TEM;

attaching a sheet of glass to the dielectric layer;

etching the silicon to a reduced thickness;

attaching a metal ring to the silicon whereby said ring surrounds, without covering, said marks;

removing the sheet of glass; and using an ion mill, removing silicon from a region surrounded by the marks, thereby thinning the silicon at the location that is to be examined by TEM.

2. The method of claim 1 wherein the dielectric is silicon oxide or silicon nitride.

3. The method of claim 1 wherein the step of etching the dielectric further comprises chemical mechanical polishing.

4. The method of claim 1 wherein the step of selectively removing all exposed polysilicon further comprises etching in a polysilicon etcher for between about 10 and 15 seconds at a temperature of about 25° C.

5. The method of claim 1 wherein the step of making marks further comprises using a laser.

6. The method of claim 5 wherein said laser is a Green Laser operated at a power level between about 100 and 200 watts and having a spot size between about 2 and 5 micron.

7. The method of claim 1 wherein the step of attaching a sheet of glass further comprises heating said glass to a temperature between about 100 and 150° C., spreading thereon a layer of a molten glue, pressing the sheet and glue against the dielectric layer, and allowing the sheet and the glue to cool.

8. The method of claim 7 wherein the step of removing the sheet of glass further comprises heating said glass to a temperature between about 100 and 150° C., thereby melting the glue.

9. The method of claim 1 wherein said reduced silicon thickness is between about 0.1 and 0.2 microns.

10. The method of claim 1 wherein the ring is copper or molybdenum and has an outer diameter between about 2.5 and 3.5 mm., and an inner diameter between about 1 and 2 mm.

11. A method to prepare a sample for TEM, comprising the sequential steps of:

provi ding an integrated circuit on a silicon wafer, including a layer of gate oxide on the silicon, at least two areas of field oxide, at least one polysilicon gate, said gate being located between the areas of field oxide, a layer of a dielectric over the gate oxide, the field oxide and the polysilicon gate, and a layer of a metal over the dielectric;

removing the metal layer and then etching the dielectric layer by means of chemical mechanical polishing until the polysilicon gate is exposed, while leaving all of the field oxide in place;

selectively removing all exposed polysilicon while leaving all of the gate oxide and field oxide in place;

by means of a laser, operated at a power level between about 100 and 200 watts, and having a spot size between about 2 and 5 microns, making marks on the gate oxide, said marks placed so as to surround a location to be examined using TEM;

attaching a sheet of glass to the dielectric layer;

etching the silicon to a reduced thickness that is between about 0.1 and 0.2 microns;

attaching a copper ring to the silicon whereby said ring surrounds, without covering, said marks;

removing the sheet of glass; and using an ion mill, removing silicon from a region surrounded by the marks, thereby thinning the silicon at the location that is to be examined by TEM.

12. The method of claim 11 wherein the step of selectively removing all exposed polysilicon further comprises etching in a polysilicon etcher for between about 10 and 15 seconds at a temperature of about 25° C.

13. The method of claim 11 wherein the step of attaching a sheet of glass further comprises heating said glass to a temperature between about 100 and 150° C., spreading thereon a layer of a molten glue, pressing the sheet and glue against the dielectric layer, and allowing the sheet and the glue to cool.

14. The method of claim 11 wherein the copper ring has an outer diameter between about 2.5 and 3.5 mm. and an inner diameter between about 1 and 2 mm.

15. The method of claim 11 wherein the step of removing the sheet of glass further comprises heating said glass to a temperature between about 100 and 150° C., thereby melting the glue.

16. The method of claim 11 wherein the step of using an ion mill further comprises a beam of argon ions, focussed down to an area between about 0.1 and 0.3 sq. mm. at a current level between about 10 and 30 microamps.

\* \* \* \* \*